US012761120B2

(12) United States Patent
Song et al.

(10) Patent No.: US 12,761,120 B2
(45) Date of Patent: Oct. 13, 2026

(54) AUTOMATIC COLLECTION DEVICE FOR DEW ON WILD HERBACEOUS PLANTS

(71) Applicant: China Institute of Water Resources and Hydropower Research, Beijing (CN)

(72) Inventors: Yifan Song, Beijing (CN); Denghua Yan, Beijing (CN); Yajing Lu, Beijing (CN); Rui Jiao, Hohhot (CN); Yunhao Wen, Hohhot (CN); Wei Shi, Hohhot (CN); Tianling Qin, Beijing (CN); Baisha Weng, Beijing (CN); Shanshan Liu, Beijing (CN)

(73) Assignee: China Institute of Water Resources and Hydro Power Research, Beijing (CN)

( * ) Notice: Subject to any disclaimer, the term of this patent is extended or adjusted under 35 U.S.C. 154(b) by 211 days.

(21) Appl. No.: 18/931,748

(22) Filed: Oct. 30, 2024

(65) Prior Publication Data

US 2026/0022993 A1 Jan. 22, 2026

(30) Foreign Application Priority Data

Jul. 19, 2024 (CN) ......................... 202410974681.5

(51) Int. Cl.
*G01N 1/10* (2006.01)
*G01N 33/18* (2006.01)

(52) U.S. Cl.
CPC ............... *G01N 1/10* (2013.01); *G01N 33/18* (2013.01)

(58) Field of Classification Search
CPC ................................ G01N 1/10; G01N 33/18
See application file for complete search history.

(56) References Cited

FOREIGN PATENT DOCUMENTS

CN 115307981 A * 11/2022 ............ G01N 33/18

* cited by examiner

*Primary Examiner* — Jamel E Williams
(74) *Attorney, Agent, or Firm* — Millen, White, Zelano & Branigan P.C.; William F. Nixon

(57) ABSTRACT

Provided is an automatic collection device for dew on wild herbaceous plants. The automatic collection device includes an electric lifting member, a rotary motor, an electric telescopic rod and a dew collector. The rotary motor drives the dew collector to rotate in a horizontal direction, and a rotation radius is gradually adjusted by the electric telescopic rod. During the rotation of the dew collector, after multiple comb teeth pass through the herbaceous plant, the dew on the multiple comb teeth drops on a water transfer membrane, and the dew is sent by the water transfer membrane into a water collection and guide groove for collection. After the dew collection in one circular area is completed, a tester can uniformly guide the dew into a collection bottle through a water outlet of the water collection and guide groove.

10 Claims, 2 Drawing Sheets

AUTOMATIC COLLECTION DEVICE FOR DEW ON WILD HERBACEOUS PLANTS

CROSS-REFERENCE TO RELATED APPLICATION

This patent application claims the benefit and priority of Chinese Patent Application No. 202410974681.5, entitled "AUTOMATIC COLLECTION DEVICE FOR DEW ON WILD HERBACEOUS PLANTS" filed on Jul. 19, 2024, the disclosure of which is incorporated by reference herein in its entirety as part of the present application.

TECHNICAL FIELD

The present disclosure relates to the technical field of dew collection, and in particular to an automatic collection device for dew on wild herbaceous plants.

BACKGROUND

Dew, as an important water source for herbaceous plants, soil crust, soil microorganisms and animals, has unique isotopic characteristics and rich nutrient content, especially in arid environment, and thus has important scientific research value. Organisms in the arid environment depend on the existence of dew to maintain their life activities, and the isotopic characteristics of the dew can provide important information about water cycle and environmental changes. In addition, the nutrient content in the dew is also of a great significance to the study of nutrient cycle in an ecological system.

However, as the dew is produced less and exists for a short time, there are great technical problems in effective collection under field conditions. The existing manual collection modes are often inefficient, which leads to the limitation of the depth and breadth of dew research.

SUMMARY

For the problems in the prior art, the present disclosure provides an automatic collection device for dew on wild herbaceous plants, which solves the problem of low efficiency of manual dew collection.

To achieve the objective above, the technical solution adopted by the present disclosure is as follows.

The present disclosure provides an automatic collection device for dew on wild herbaceous plants, including an electric lifting member, which is provided with a carrier stage capable of lifting in a vertical direction; a rotary motor, where the rotary motor is fixed to the carrier stage; an electric telescopic rod, where the electric telescopic rod is configured to rotate in a horizontal direction, and one end of the electric telescopic rod is fixedly connected with the rotary motor; and a dew collector, where the dew collector includes a housing fixed to an other end of the electric telescopic rod. The housing includes a bottom plate, multiple comb teeth are fixed to an outer edge of the bottom plate, a water transfer membrane is fixed between each two adjacent comb teeth of the multiple comb teeth. A water collection and guide groove is formed inside the bottom plate. A water inlet communicating with the water collection and guide groove is formed in a top surface of the bottom plate. A water outlet of the water collection and guide groove is formed in a side of the bottom plate, and the water transfer membrane is configured to transfer the dew on the herbaceous plants into the water collection and guide groove.

The operation principle of this solution is as follows. After determining a collection place of the dew of the herbaceous plants, a height suitable for collecting dew is first determined according to the heights of the herbaceous plants, then a height of the dew collector is adjusted through the electric lifting member. Afterwards, the rotary motor is started, which drives the dew collector to rotate in a horizontal direction, and the rotation radius can be gradually adjusted by the electric telescopic rod. During the rotation of the dew collector, after the multiple comb teeth pass through the herbaceous plants, the dew on the multiple comb teeth drops on the water transfer membrane, and the dew is sent by the water transfer membrane into the water collection and guide groove for collection. After the dew collection in one circular area is completed, a tester can uniformly guide the dew into a collection bottle through the water outlet of the water collection and guide groove.

Further, a middle portion of each water transfer membrane is provided with a V-shaped opening, and the V-shaped opening faces a tip of each of the multiple comb teeth. The arrangement of the V-shaped opening enables an end of the herbaceous plant to enter the opening, and both ends of the opening of the water transfer membrane are respectively located at both sides of the herbaceous plant. Therefore, when the water transfer membrane skips and bends the end of the herbaceous plant, both sides of the water transfer membrane can receive the dew, and the receiving area is increased.

Further, a hydrophilic coating or a bionic-lotus-leaf layer is arranged on a surface of each water transfer membrane. The hydrophilic coating may be a hydrophilic silicon oxide coating or titanium oxide coating. The bionic-lotus-leaf layer is a bionic material based on superhydrophobic characteristics of the surface of the lotus leaf. By imitating a micro-nano structure of the surface of the lotus leaf, this material makes the dew form a high contact angle on its surface, thus showing a ball shape and having excellent water conductivity.

Further, multiple dew inlets below the water transfer membrane are provided at an outer end of the bottom plate, each of the multiple dew inlets communicates with a corresponding one of the multiple flow channels, and an other end of each of the multiple flow channels is inclined downwards and communicates with the water collection and guide groove. Due to the characteristics of the dew and the water transfer membrane, the dew can slide into the flow channel along a lower surface of the water transfer membrane by surface tension, thus increasing the collection of the dew.

Further, a top projection of each of the multiple dew inlets is funnel-shaped, each of the multiple flow channels is of a Tesla valve structure, and a branch tube of each of the multiple flow channels is a capillary tube. The dew collected in the flow channel of the dew collector may spill out of the flow channel due to inertia when the rotary motor is stopped, but the flow channel with the Tesla valve structure, which does not affect the flow velocity of dew collection and has the characteristics of a one-way valve, can prevent the gathered dew from spilling out from the flow channel. In the process of collecting the dew, even if the dew is too little to fill the flow channel, the single dew in the form of water droplets can move into the water collection and guide groove along multiple capillary tubes on the flow channel in turn under the capillary action and the relative movement of the dew collector.

Further, a switch plate is slidingly arranged on one side, communicating with multiple flow channels, of the water collection and guide groove, the switch plate is provided with communicating ports in one-to-one correspondence to the multiple flow channels, and all of the multiple flow channels are closed or opened by sliding the switch plate. Considering that the dew on the bottom plate may be polluted by dust and impurities, the switch plate can be adopted to close the flow channel first. Due to the arrangement of the Tesla structure, the flow channel can be configured for buffering part of the dew without spilling the dew. Therefore, during the collection of the dew, the dew flowing through the bottom plate can be collected first through the water collection and guide groove, and then the switch plate can be opened to collect dew flowing out from the flow channel separately, which can reduce the risk of dew pollution and facilitate the comparison of experimental data of different dew.

Further, a communicating port of each of the multiple flow channels communicating with the water collection and guide groove is provided with a detachable end cover, and the water inlet of the water collection and guide groove is provided with a cover plate for reducing dew evaporation. The arrangement of the end cover facilitates to collect the dew in the multiple flow channels separately, thus further increasing the comparative test data of the dew.

Further, a camera for detecting heights of the herbaceous plants is arranged at a position, adjacent to the dew collector, of the electric telescopic rod, and the camera is electrically connected with a controller. The camera can obtain the information of the herbaceous plants through image recognition and feed the information back to the controller, and the controller can control the height of the electric lifting member and the length of the electric telescopic rod through visual information fed back by the camera. For example, when the height of one herbaceous plant is too high, the controller can control the electric lifting member to raise the dew collector to avoid the collision of the dew collector.

Further, the electric lifting member is an electric push rod vertically fixed to a base, and the electric push rod and the electric telescopic rod are both electrically connected with the controller.

Further, a superhydrophobic coating is arranged on a top surface of the bottom plate. The arrangement of the ultra-hydrophobic coating is conducive to the dew to move along the top surface of the bottom plate.

The present disclosure provides the automatic collection device for dew on wild herbaceous plants, which has the beneficial effects as follows.

1. The device can automatically collect dew on the herbaceous plants in a circular area, which speeds up the collection efficiency and can save time and labor compared with the manual collection. The rotary motor drives the dew collector to rotate in a horizontal direction, and a rotation radius is gradually adjusted by the electric telescopic rod. During the rotation of the dew collector, after multiple comb teeth pass through the herbaceous plants, the dew on the multiple comb teeth drops on the water transfer membrane, and the dew is sent by the water transfer membrane into the water collection and guide groove for collection. After the dew collection in one circular area is completed, a tester can uniformly guide the dew into a collection bottle through the water outlet of the water collection and guide groove.

2. By providing multiple flow channels with the Tesla valve structure, the dew can be prevented from spilling out from the flow channels when the dew collector slows down or stops. Moreover, the flow channels can serve as containers for buffering dew separately, which not only reduces the risk of dew pollution, but also facilitates the formation of multiple groups of comparative experimental data.

Figure 1:
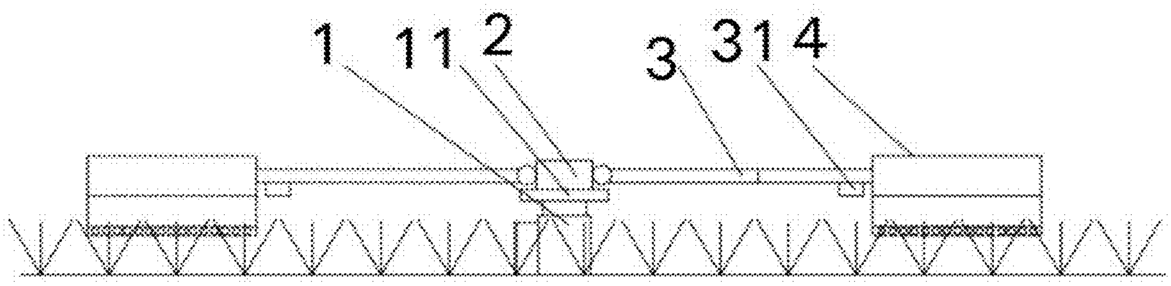
FIG. 1 is a structural diagram of an automatic collection device for dew on wild herbaceous plants.

List of reference characters: 1 electric lifting member; 11 carrier stage; 2 rotary motor; 3 electric telescopic rod; 31 camera; 4-dew collector; 41 comb tooth; 42 water transfer membrane; 43 bottom plate; 431 dew inlet; 432 flow channel; 433 switch plate; 44 water collection and guide groove.

DETAILED DESCRIPTION OF THE EMBODIMENTS

The specific embodiments of the present disclosure are described below to facilitate those skilled in the art to understand the present disclosure. However, it should be clear that the present disclosure is not limited to the scope of the specific embodiments. As long as various changes are within the spirit and scope of the present disclosure defined and determined by the appended claims, these changes are apparent to those of ordinary skill in the art, and all inventions and creations using the concept of the present disclosure are protected.

Referring to FIG. 1, this embodiment provides an automatic collection device for dew on wild herbaceous plants, including an electric lifting member 1, a rotary motor 2, an electric telescopic rod 3 and a dew collector 4.

The electric lifting member 1 is provided with a carrier stage 11 capable of lifting in a vertical direction. In this embodiment, the electric lifting member 1 is an electric push rod vertically fixed to a base, and the electric push rod and the electric telescopic rod 3 are both electrically connected with a controller.

The rotary motor 2 is fixed to the carrier stage 11, and is configured to drive the dew collector 4 to rotate.

The electric telescopic rod 3 is configured to rotate in a horizontal direction, one end of the electric telescopic rod 3 is fixedly connected with the rotary motor 2, and the other end of the electric telescopic rod 3 is configured to fix the dew collector 4.

Figure 2:
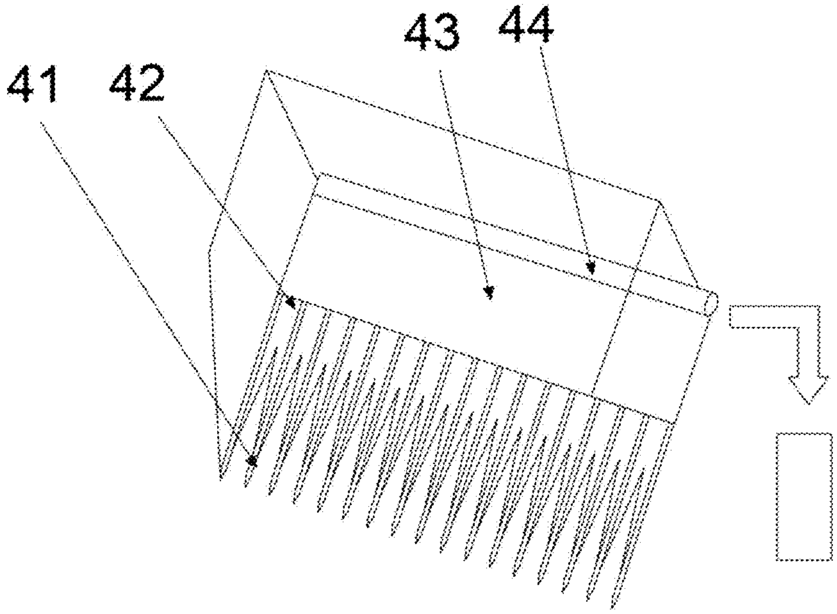
FIG. 2 is a structural diagram of a dew collector.

Referring to FIG. 2, the dew collector 4 is configured to collect the dew, and includes a housing. The housing includes a bottom plate 43, multiple comb teeth 41 are fixed to an outer edge of the bottom plate 43, and a water transfer membrane 42 is fixed between each two adjacent comb teeth 41. A water collection and guide groove 44 is formed inside the bottom plate 43, and a water inlet communicating with the water collection and guide groove 44 is formed in a top surface of the bottom plate 43. A cover plate for reducing dew evaporation is arranged at the water inlet of the water collection and guide groove 44, a water outlet of the water collection and guide groove is formed in a side of the bottom plate 43, and the water transfer membrane 42 is configured to transfer the dew on the herbaceous plants into the water collection and guide groove 44.

In this embodiment, to facilitate the transferring of the dew, a hydrophilic coating or a bionic-lotus-leaf layer is arranged on a surface of each water transfer membrane 42, and a superhydrophobic coating is arranged on a top surface of the bottom plate 43. The superhydrophobic coating is provided to facilitate the dew to move along the top surface of the bottom plate 43. In this embodiment, the hydrophilic coating may be a hydrophilic silicon oxide coating or a titanium oxide coating. The bionic-lotus-leaf layer is a bionic material based on superhydrophobic characteristics of the surface of the lotus leaf. By imitating a micro-nano structure of the surface of the lotus leaf, this material makes the dew form a high contact angle on its surface, thus showing a ball shape and having excellent water conductivity.

In order to increase the area of the water transfer membrane 42 for receiving the dew, a middle portion of each water transfer membrane 42 is provided with a V-shaped opening, and the V-shaped opening faces a tip of each comb tooth 41. The arrangement of the V-shaped opening enables an end of the herbaceous plant to enter the opening, and both ends of the opening of the water transfer membrane 42 are respectively located at both sides of the herbaceous plant. Therefore, when the water transfer membrane 42 skips and bends the end of the herbaceous plant, both sides of the water transfer membrane 42 can receive the dew, and the receiving area is increased.

Figure 3:
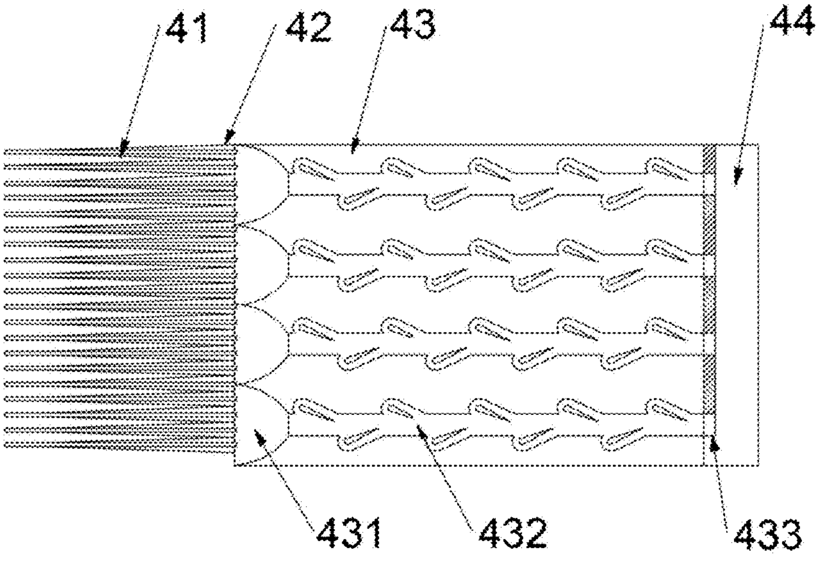
FIG. 3 is a structural diagram of an internal flow channel of a bottom plate.
Figure 4:
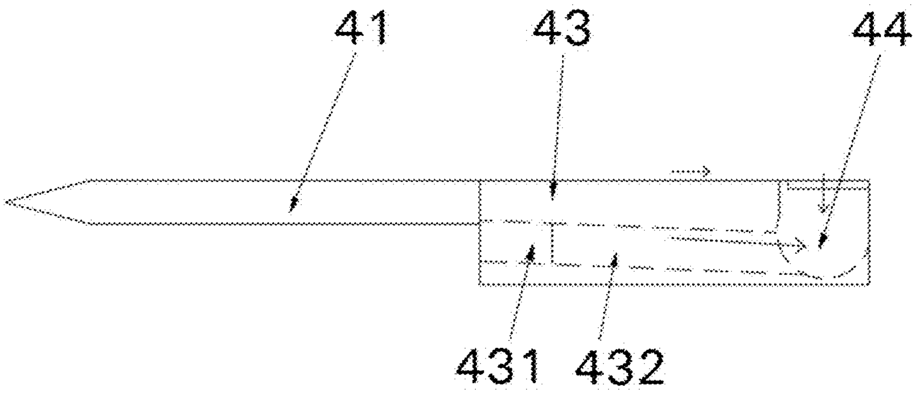
FIG. 4 is a structural diagram of the internal flow channel which is opened of the bottom plate.
Figure 5:
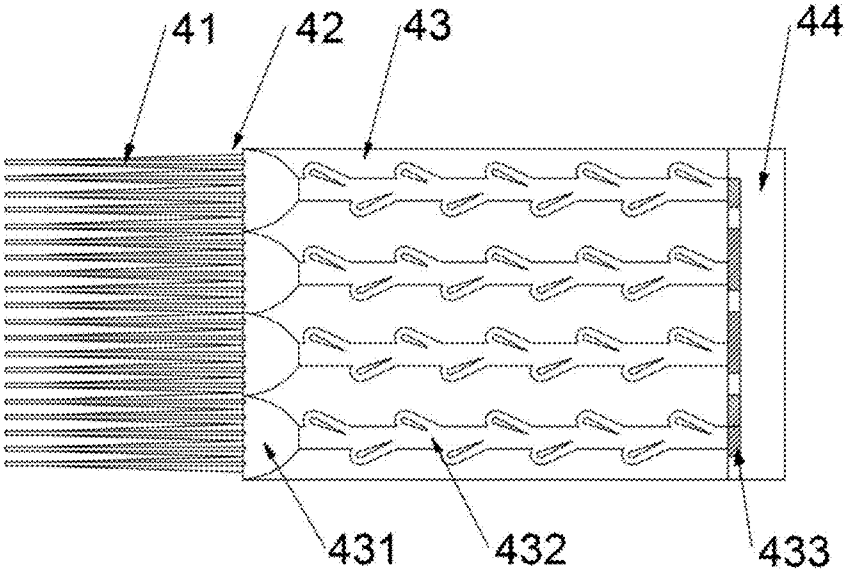
FIG. 5 is a structural diagram of the internal flow channel which is closed of the bottom plate.
Figure 6:
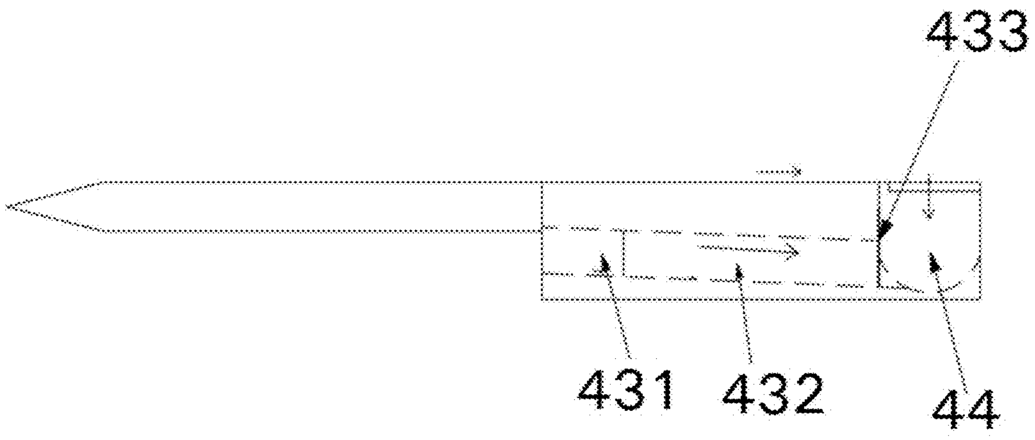
FIG. 6 is a side view of the internal flow channel which is closed of the bottom plate.

In order to improve the collection amount of the dew, referring to FIG. 2 and FIG. 3, multiple dew inlets 431 below the water transfer membrane 42 are provided at an outer end of the bottom plate 43, each dew inlet 431 communicates with one flow channel 432, and the other end of the flow channel 432 is inclined downwards and communicates with the water collection and guide groove 44. Due to the characteristics of the dew and the water transfer membrane 42, the dew can slide into the flow channel along a lower surface of the water transfer membrane 42 by surface tension, thus increasing the collection of the dew.

As a further structure of the flow channel 432, a top projection of each dew inlet 431 is funnel-shaped, each flow channel 432 is of a Tesla valve structure, and a branch tube of each flow channel 432 is a capillary tube. The dew collected in the flow channel 432 of the dew collector 4 may spill out of the flow channel 432 due to inertia when the rotary motor 2 is stopped, but the flow channel 432 with the Tesla valve structure, which does not affect the flow velocity of dew collection and has the characteristics of a one-way valve, can prevent the gathered dew from spilling out from the flow channel 432. In the process of collecting the dew, even if the dew is too little to fill the flow channel 432, the single dew in the form of water droplets can move into the water collection and guide groove 44 along multiple capillary tubes on the flow channel 432 in turn under the capillary action and the relative movement of the dew collector 4.

In order to reduce the risk of dew pollution, referring to FIG. 3 to FIG. 6, a switch plate 433 is slidingly arranged on one side, communicating with the multiple flow channels 432, of the water collection and guide groove 44, the switch plate 433 is provided with communicating ports in one-to-one correspondence to the multiple flow channels 432, and all flow channels 432 are closed or opened by sliding the switch plate 433. Considering that the dew on the bottom plate 43 may be polluted by dust and impurities, the switch plate 433 can be adopted to close the flow channel 432 first. Due to the arrangement of the Tesla structure, the flow channel 432 can be configured for buffering part of the dew without spilling the dew. Therefore, during the collection of the dew, the dew flowing through the bottom plate 43 can be collected first through the water collection and guide groove 44, and then the switch plate 433 can be opened to collect dew flowing out from the flow channel 432 separately, which can reduce the risk of dew pollution and facilitate the comparison of experimental data of different dew.

As another solution of this embodiment, in order to collect the dew in each flow channel 432 separately, the communicating port of each flow channel 432 and the water collection and guide groove 44 is provided with a detachable end cover. The arrangement of the end covers facilitates to collect the dew in the multiple flow channels 432 separately, thus further increasing the comparative test data of the dew.

As a further solution of this embodiment, in order to avoid the collision of the dew collector 4, a camera 31 for detecting a height of the herbaceous plant is arranged at a position, close to the dew collector 4, of the electric telescopic rod 3, and the camera is electrically connected with a controller. The camera can obtain the information of the herbaceous plants through image recognition and feed the information back to the controller, and the controller can control the height of the electric lifting member 1 and the length of the electric telescopic rod 3 through visual information fed back by the camera. For example, when the height of one herbaceous plant is too high, the controller can control the electric lifting member 1 to raise the dew collector 4 to avoid the collision of the dew collector 4.

In order to facilitate remote observation by a tester, the controller is electrically connected with a communication module, and the communication module transmits the information of the camera to a control terminal. The tester can directly and manually control the height of the electric lifting member 1 and the length of the electric telescopic rod 3, and can directly and remotely control the dew collection at a specific time point, thus improving the operability of the automatic dew collection device for the wild herbaceous plant.

In conclusion, the operation principle of the technical solution is as follows.

After determining a collection place of the dew of the herbaceous plants, a height suitable for collecting dew is first determined according to the heights of the herbaceous plants, then the height of the dew collector 4 is adjusted through the electric lifting member 1. Afterwards, the rotary motor 2 is started, which drives the dew collector 4 to rotate in a horizontal direction, and the rotation radius is gradually adjusted by the electric telescopic rod 3. During the rotation of the dew collector 4, after multiple comb teeth 41 pass through the herbaceous plant, the dew on the multiple comb teeth 41 drops on the water transfer membrane 42, and the water transfer membrane 42 sends the dew on the upper surface and the lower surface onto the bottom plate 43 and into the flow channel 432, respectively, the dew on the bottom plate 43 and in the flow channel 432 flows into the water collection and guide groove 44 for collection. After the dew collection in one circular area is completed, the tester can uniformly guide the dew into a collection bottle through the water outlet of the water collection and guide groove 44.

In order to prevent the dew on the bottom plate 43 from being polluted by impurities, the tester can collect the dew on the bottom plate 43 and in the flow channel 432 separately.

Although the specific embodiments of the present disclosure have been described in detail with the accompanying drawings, it should not be construed as the limitation of the scope of protection of this patent. Within the scope described in the claims, various modifications and deformations that can be made by those skilled in the art without creative labor still belong to the scope of protection of this patent.

What is claimed is:

1. An automatic collection device for dew on wild herbaceous plants, comprising:

an electric lifting member (1), wherein the electric lifting member (1) is provided with a carrier stage (11) capable of lifting in a vertical direction;

a rotary motor (2), wherein the rotary motor (2) is fixed to the carrier stage (11);

an electric telescopic rod (3), wherein the electric telescopic rod (3) is configured to rotate in a horizontal direction, and one end of the electric telescopic rod (3) is fixedly connected with the rotary motor (2); and a dew collector (4), wherein the dew collector (4) comprises a housing fixed to an other end of the electric telescopic rod (3), the housing comprises a bottom plate (43), a plurality of comb teeth (41) are fixed to an outer edge of the bottom plate (43), a water transfer membrane (42) is fixed between each two adjacent comb teeth (41) of the plurality of comb teeth (41), a water collection and guide groove (44) is formed inside the bottom plate (43), a water inlet communicating with the water collection and guide groove (44) is formed in a top surface of the bottom plate (43), a water outlet of the water collection and guide groove is formed in a side of the bottom plate (43), and the water transfer membrane (42) is configured to transfer the dew on the herbaceous plants into the water collection and guide groove (44).

2. The automatic collection device for dew on wild herbaceous plants according to claim 1, wherein a middle portion of each water transfer membrane (42) is provided with a V-shaped opening, and the V-shaped opening faces a tip of each of the plurality of comb teeth (41).

3. The automatic collection device for dew on wild herbaceous plants according to claim 2, wherein a hydrophilic coating or a bionic-lotus-leaf layer is arranged on a surface of each water transfer membrane (42).

4. The automatic collection device for dew on wild herbaceous plants according to claim 1, wherein a plurality of dew inlets (431) below the water transfer membrane (42) are provided at an outer end of the bottom plate (43), each of the plurality of dew inlets (431) communicates with a corresponding one of a plurality of flow channels (432), and an other end of each of the plurality of flow channels (432) is inclined downwards and communicates with the water collection and guide groove (44).

5. The automatic collection device for dew on wild herbaceous plants according to claim 4, wherein a top projection of each of the plurality of dew inlets (431) is funnel-shaped, each of the plurality of flow channels (432) is of a Tesla valve structure, and a branch tube of each of the plurality of flow channels (432) is a capillary tube.

6. The automatic collection device for dew on wild herbaceous plants according to claim 4, wherein a switch plate (433) is slidingly arranged on one side, communicating with the plurality of flow channels (432), of the water collection and guide groove (44), the switch plate (433) is provided with communicating ports in one-to-one correspondence to the plurality of flow channels (432), and all of the plurality of flow channels (432) are closed or opened by sliding the switch plate (433).

7. The automatic collection device for dew on wild herbaceous plants according to claim 4, wherein a communicating port of each of the plurality of flow channels (432) communicating with the water collection and guide groove (44) is provided with a detachable end cover, and the water inlet of the water collection and guide groove (44) is provided with a cover plate for reducing dew evaporation.

8. The automatic collection device for dew on wild herbaceous plants according to claim 1, wherein a camera for detecting heights of the herbaceous plants is arranged at a position, adjacent to the dew collector (4), of the electric telescopic rod (3), and the camera is electrically connected with a controller.

9. The automatic collection device for dew on wild herbaceous plants according to claim 8, wherein the electric lifting member (1) is an electric push rod vertically fixed to a base, and the electric push rod and the electric telescopic rod (3) are both electrically connected with the controller.

10. The automatic collection device for dew on wild herbaceous plants according to claim 1, wherein a superhydrophobic coating is arranged on a top surface of the bottom plate (43).

* * * * *